United States Patent
Denzer et al.

(10) Patent No.: US 6,803,050 B2
(45) Date of Patent: Oct. 12, 2004

(54) TRANSPARENT AQUEOUS COMPOSITIONS COMPRISING HYDROPHOBIC SILICONE OILS

(75) Inventors: Horst Denzer, Düsseldorf (DE); Hiroshi Abe, Barcelona (ES); Monika Pytlik, Duisburg (DE); Rosemarie Jansen, Emmerich/Elten (DE); Andrea Buhmann, Koblenz (DE)

(73) Assignee: Kao Chemicals Europe S.L., Barcelona (ES)

( * ) Notice: Subject to any disclaimer, the term of this patent is extended or adjusted under 35 U.S.C. 154(b) by 0 days.

(21) Appl. No.: 10/399,239

(22) PCT Filed: Oct. 26, 2001

(86) PCT No.: PCT/EP01/12436

§ 371 (c)(1),
(2), (4) Date: Jul. 9, 2003

(87) PCT Pub. No.: WO02/36082

PCT Pub. Date: May 10, 2002

(65) Prior Publication Data

US 2004/0014879 A1 Jan. 22, 2004

(30) Foreign Application Priority Data

Oct. 30, 2000 (DE) .......................................... 100 53 728

(51) Int. Cl.⁷ .............................................. A61K 7/075
(52) U.S. Cl. .................... 424/401; 424/70.12; 524/588
(58) Field of Search ............................. 424/401, 70.12; 524/588

(56) References Cited

U.S. PATENT DOCUMENTS

| | | | |
|---|---|---|---|
| 4,933,176 A | | 6/1990 | van Reeth |
| 4,954,335 A | * | 9/1990 | Janchipraponvej ....... 424/70.28 |
| 5,078,990 A | * | 1/1992 | Martin et al. ............... 510/124 |
| 6,013,683 A | | 1/2000 | Hill et al. |

FOREIGN PATENT DOCUMENTS

| | | |
|---|---|---|
| EP | 0 814 753 | 1/1998 |
| EP | 0 820 758 | 1/1998 |

\* cited by examiner

*Primary Examiner*—Margaret G. Moore
(74) *Attorney, Agent, or Firm*—Nath & Associates PLLC; Gary M. Nath; Joshua B. Goldberg

(57) ABSTRACT

The invention relates to optically transparent aqueous compositions containing hydrophobic silicone oil and a comparably low amount of wash-active matter, being suitable as a hair treatment composition such as a shampoo. In particular, it provides an optically transparent aqueous composition comprising (a) a hydrophobic silicone oil in an amount of 1–3 wt.-% with respect to the total weight of the composition; (b) a solubilizer for the silicone oil; and (d) an anionic surfactant; wherein the weight-ratio of component (b) to component (a) is in the range of 1:1 to 12:1; and wherein the total amount of the components (b) and (c) is in the range of 10–25 wt.-% with respect to the total weight of the composition. The invention also provides a method for preparing the above composition.

18 Claims, No Drawings

TRANSPARENT AQUEOUS COMPOSITIONS COMPRISING HYDROPHOBIC SILICONE OILS

The present invention relates to optically transparent aqueous compositions containing hydrophobic silicone oil and a comparably low amount of wash-active matter, the compositions being suitable as a hair treatment composition such as a shampoo.

Due to their very low surface tension, the spreadability of silicone oils on most surfaces such as ceramics, textiles, paper, skin, and hair, is excellent. In the field of personal care products, silicone oils are used because of their hair and skin smoothing properties, hair gloss enhancing properties and skin feel improving (non-oily, silky skin feel) properties. For many decades they are therefore ingredients in hairsprays, conditioners, colorants and sun protecting creams. In cosmetic rinse-off products like shampoos they appeared in the 1980ies and could obtain a considerable market share in the early 1990ies in the so-called "two-in-one" shampoos. These shampoos contain emulsified silicone oils. Silicone oil emulsions, however, show problems with respect to compatibility and stability, they show a strong foaminess reducing effect and furthermore they are generally not transparent. This is why hydrophilic silicone polyethers have been introduced into the market. But apart from their generally higher price, the conditioning effect of hydrophilic silicone polyethers on skin and hair is generally much lower than of the hydrophobic silicone oils.

In view of these problems, attempts have been made to provide aqueous compositions containing hydrophobic silicone oil, the silicone oil being in a solubilized or microemulsified state. U.S. Pat. No. 6,013,683 describes a microemulsion containing 40 to 95 wt. % of a short chain linear siloxane and water, and 5 to 60 wt. % of non-ionic and/or cationic surfactants. However, the microemulsions disclosed in this patent are only transparent in a very narrow temperature range and easily become turbid when added to aqueous solutions.

EP 0 529 883 B1 discloses hair shampoo compositions containing sodium lauryl ether sulfate and cocoamido propyl betaine as surfactants and 1.0 wt.-% of silicone oil. The silicone oil was added as micro-emulsion prepared by an emulsion polymerization technique. Hence, EP 0 529 883 B1 does not disclose aqueous compositions containing silicone oil which may be easily prepared.

On the other hand, the inventors of the present invention previously published a method allowing the easy incorporation of silicone oil into shampoos (H. Denzer, R. Jansen, M. Reininghaus in "Parfümerie und Kosmetik"; June 1999 pages 18–20). However, the method only allowed for the incorporation of comparably low amounts of silicone oil such as 0.5 wt.-% when using wash-active matter within the range of 15–40 wt.-%. Higher amounts of hydrophobic silicone oil could only be solubilized by increasing the amount of wash-active matter which is, however, not acceptable for dermatological and environmental reasons as well as for price reasons.

In view of these drawbacks of the prior art, it is the object underlying the present invention to provide an easily preparable, optically transparent aqueous composition being suitable as hair shampoo containing an increased amount of hydrophobic silicone oil.

This object of the present invention is solved by the provision of an optically transparent aqueous composition comprising (a) a hydrophobic silicone oil in an amount of 1–3 wt.-% with respect to the total weight of the composition;

(b) a solubilizer for the silicone oil; and (c) an anionic surfactant;

wherein the weight ratio of component (b) to component (a) is in the range of 1:1 to 10:1; and wherein the total amount of the components (b) and (c) is in the range of 10–25 wt.-% with respect to the total weight of the composition.

A hydrophobic silicone oil is generally a silicone oil which is soluble in paraffinic oil at 25° C. Hydrophobic silicone oils to be used according to the present invention include both volatile and non-volatile silicone oils.

Specific examples include a cyclic methyl siloxane having the formula $\{(CH_3)_2SiO\}_x$ in which x is 3–6, or short chain linear methyl siloxanes having the formula

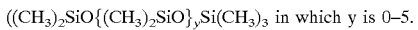
$((CH_3)_3SiO\{(CH_3)_2SiO\}_ySi(CH_3)_3$ in which y is 0–5.

Some suitable cyclic methyl siloxanes are hexamethylcyclotrisiloxanes ($D_3$), a solid with a boiling point of 134° C. and the formula $\{(Me_2)SiO\}_3$; octamethylcyclotetrasiloxane ($D_4$) with a boiling point of 176° C., a viscosity of 2.3 mm$^2$/s, and the formula $\{(Me_2)SiO\}_4$; decamethylcyclopentasiloxane ($D_5$) (cyclomethicone) with a boiling point of 210° C., a viscosity of 3.87 mm$^2$/s, and the formula $\{(Me_2)SiO\}_5$; and dodecamethylcyclohexasiloxane ($D_6$) with a boiling point of 245° C., a viscosity of 6.62 mm$^2$/s and the formula $\{(Me_2)SiO\}_6$.

Some suitable short linear methyl siloxane are hexamethyldisiloxane (MM) with a boiling point of 100° C., viscosity of 0–65 mm$^2$/s, and formula $Me_3SiOMe_3$; octamethyltrisiloxane (MDM) with a boiling point of 152° C., viscosity of 1.04 mm$^2$/s, and formula $Me_3SiOMe_2SiOsiMe_3$; decamethyltetrasiloxane ($MD_2M$) with a boiling point of 194° C., viscosity of 1.53 mm$^2$/s, and formula $Me_3SiO(MeSiO)_2SiMe_3$; dodecamethylpentasiloxane ($MD_3M$) with a boiling point of 229° C., viscosity of 2.06 mm$_2$/s; and formula $Me_3SiO(Me_2SiO)_3SiMe_3$; tetradecamethylhexasiloxane ($MD_4M$) with a boiling point of 245° C., viscosity of 2.63 mm2/s, and formula $Me_3SiO(Me_2SiO)_4SiMe_3$; and hexadecamethylheptasiloxane ($MD_5M$) with a boiling point of 270° C., viscosity of 3.24 mm$^2$/s, and formula $Me_3SiO(Me_2SiO)_5SiMe_3$.

Furthermore, long chain linear siloxanes such as phenyltrimethicone, bis(phenylpropyl)dimethicone, dimethicone, and dimethiconol are also included.

The amount of the hydrophobic silicone oil is 1–3 wt.-%, preferably 1.5 wt. % to 3 wt. % with respect to the total weight of the composition.

The composition of the present invention further contains a solubilizer for the silicone oil. The term "solubilizer", in the context of the present invention, refers to a surfactant which allows the solubilization of the hydrophobic silicone oil or the formation of a micro-emulsion of the hydrophobic silicone oil in an aqueous phase. Solubilization is defined as the spontaneous dissolving of a substance by the reversible interaction with the micelles of a surfactant in a solvent to form a thermodynamically stable isotropic solution with reduced thermodynamic activity of the solubilized material (see "Surfactants and Interfacial Phenomena", by Milton T. Rosen, ed. John Wiley & Sons (1978), Chapter 4, page 123). This isotropic solution is generally a single phase clear microemulsion which forms spontaneously in the sense that it does not require a high energy input by means of high shear devices. Thus, a turbine, impeller, colloid mill, homogenizer, or sonicator, is not required to form these systems. It is only necessary that the appropriate amounts of the three components water, silicone oil, and solubilizer be added to a suitable container, and the container is either hand shaken, or gently stirred by means of a laboratory magnetic stirrer at a temperature below 30° C. Of course, the components can be mixed or sheared with more energy input, and the clear single phase system will still be obtained, but no advantage results from such additional energy usage.

The solubilization property of a surfactant or surfactant mixture can be easily determined by placing the surfactant/surfactant mixture, silicone oil, such as Cyclomethicone and possibly water in a vessel, e.g. in a total volume of 100 ml. The weight ratio of solubilizer to silicone oil may be in the range of 1:1 to 12:1. Then, a magnetic bar is introduced into the vessel, and the vessel is placed on top of a magnetic stirrer such as IKAMAG (supplied by Janke&Kunkel, Germany). Subsequently, the mixture is stirred at a maximum of 400 RPM, preferably 200 RPM at a temperature of 20° C. or less for some minutes, e.g. 5 minutes. 400 RPM correspond approximately to an energy input of 50 W. If the mixture thus obtained has formed an optically transparent homogeneous solution, the surfactant/surfactant mixture is useful as a solubilizer according to the present invention.

The solubilizer to be used according to the present invention is preferably a cryptoanionic surfactant, a non-ionic surfactant, a mixture of a non-ionic surfactant with an amphoteric surfactant, or a mixture of a non-ionic surfactant with a cryptoanionic surfactant. A mixture of a non-ionic surfactant with an amphoteric surfactant or a cryptoanionic surfactant is particularly preferable. The term "cryptoanionic surfactant" describes anionic surfactants having both anionic and non-ionic properties, as the anionic character is hidden by complexation. The anionic/non-ionic properties are generally influenced by the pH value.

Preferred solubilizers include surfactants having at least one hydrophobic moiety composed of an alkyl chain or acyl chain having 6 to 22 carbon atoms and at least one hydrophilic moiety composed of an oligoethylene oxide chain. Particularly preferred surfactants comprise alkyl ethers or polyglycol ethers from amides derived from carboxylic acids or ether carboxylic acid, ethoxylated glycerides derived from carboxylic acids having 6 to 22 carbon atoms and/or alkyl ether carboxylates derived from alkanols having 6 to 22 carbon atoms.

As a non-ionic solubilizer, ethoxylated glycerides derived from carboxylic acids having 6 to 22 carbon atoms are preferred including compounds of the following formula (I):

Formula (I):

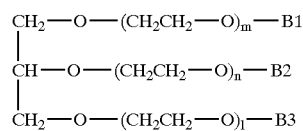

wherein each of m, n, and l independently represent a number from 0 to 40, the sum of m, n and l being in the range of 1 to 200, preferably 9 to 19; and B1, B2, and B3 independently represent H or an acyl residue having 6 to 22 carbon atoms, with the proviso that at least one of B1, B2 and B3 is an acyl residue having 6to 22 carbon atoms.

The ethoxylated glyceride to be used as solubilizer is desirably used as a mixture of compounds of the above formula (I) comprising
(i) compounds represented by the above formula (I), wherein each of B1, B2 and B3 independently represent an acyl group having 6 to 22 carbon atoms;
(ii) compounds represented by the above formula (I), wherein two of B1, B2 and B3 independently represent an acyl group having 6 to 22 carbon atoms, the remainder representing H;
(iii) compounds represented by the above formula (I), wherein one of B1, B2 and B3 represents an acyl group having 6 to 22 carbon atoms; the remainder representing H;
(iv) compounds represented by the following formula (I), wherein each of B1, B2 and B3 represent H;
the weight ratio of the compounds (i)/(ii)/(iii) being 1 to 15/9 to 35/46 to 90.

These compounds are preferably prepared by a reaction between triglyceride and glycerine and ethylene oxide. The preparation of these compounds is described in detail in the European Patent EP 0 586 323 B1 and in the European Patent Application No. 99 106 233.2.

The acyl group having 6 to 22 carbon atoms, desirably 12 to 18 carbon atoms, is preferably derived from a natural fat or oil or a synthetic glyceride. Preferred fats and oils include vegetable palm kernel oil, sunflower oil, rapeseed oil, castor oil, olive oil, soybean oil; and animal fat such as tallow, bone oil; fish oil, hardened oils and semihardened oils thereof; and mixtures thereof. Particularly preferred are acyl groups derived from coconut oil, palm oil and tallow such as beef tallow.

A particularly preferred ethoxylated glyceride is glycereth-17 cocoate, marketed under the trade name Levenol C-201 by Kao S. A. This is a mixture of compounds of the above formula (I) wherein the sum of m, n, and l is 17 and either one or two groups of B1 and B2 are acyl groups derived from coconut oil.

Furthermore, it is preferred to use the ethoxylated glyceride in combination with an amphoteric surfactant such as lauryl hydroxysultaine.

Examples for cryptoanionic surfactants include alkyl ether carboxylate derived from alkanols having 6 to 22 carbon atoms, preferably those satisfying the following formula (II):

Formula (II):

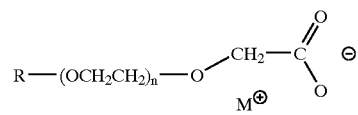

wherein R is an alkyl residue having 6 to 22 carbon atoms, n has a value in the range of 5 to 15, more preferably 7 to 10, and $M^+$ is an appropriate cation, preferably an alkaline metal cation such as sodium or potassium.

Particularly preferred are compounds of the above formula (II) wherein R is an alkyl residue having 8 to 16, more desirably 12 to 14 carbon atoms.

Alkyl ether carboxylates are preferably used as liquid concentrated aqueous solutions additionally containing nonionic surfactants such as ethoxylated products derived from polyhydric alcohols, such as glycerine, that is, compounds of the above formula (I) wherein each of B1, B2 and B3 represent a hydrogen atom, and/or containing alcohol ethoxylates, preferably of the formula $R(OCH_2CH_2)_nOH$, wherein R and n have the same meaning as defined above for formula (II). Most preferred are Sodium Laureth-8 Carboxylate (marketed under the trade name ÂKYPO SOFT 70 NV by Kao Chemicals Europe), a mixture comprising Sodium Laureth-8 Carboxylate and Laureth-7 (marketed under the trade name ÂKYPO SOFT 70 BVC by Kao Chemicals Europe), and a mixture comprising 30 to 40 wt. % Sodium Laureth-11 Carboxylate, 20 to 30 wt. % Laureth-10 and 5 to 10 wt. % ethoxylated glycerine and carboxymethylated products thereof, the balance being water and sodium chloride (marketed under the trade name AKYPO SOFT 100 BVC by Kao Chemicals Europe). The preparation of corresponding mixtures is described in EP 0 580 263 B1.

Furthermore, preferred solubilizers according to the present invention include compounds of the following formula (III) (alkyl ethers or polyglycol ethers from amides derived from carboxylic acids or ether carboxylic acids)

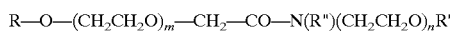

R—O—(CH$_2$CH$_2$O)$_m$—CH$_2$—CO—N(R")(CH$_2$CH$_2$O)$_n$R' wherein R is an alkyl group or alkenyl group having 6 to 22, preferably 12 to 18, more preferably 13 to 15 carbon atoms; R' is a hydrogen atom or an alkyl group or alkenyl group having 6 to 22, preferably 12 to 18, more preferably 13 to 15 carbon atoms; R" is a hydrogen atom or an alkyl group having 1 to 5 carbon atoms which is optionally hydroxylated, preferably a hydrogen atom, a methyl group, an ethyl group or a hydroxyethyl group; m has a value in the range of 1 to 10, preferably 1 to 3, most preferably 2; and n has a value in the range of 0 to 10, preferably 0 to 5.

These compounds are commercially available and are generally sold under the name Aminol.

Particularly preferred are compounds of the formula (III) wherein m is 2, n is 1, R represents an alkyl group having 13 to 15 carbon atoms; and both R' and R" represent a hydrogen atom.

Most preferred as compounds of the formula (III) is a composition marketed under the name Aminol A15 which is trideceth-2 carboxamide MEA.

According to the present invention, it is particularly preferred to use the compounds of the formula (III) in combination with the amphoteric or cryptoanionic surfactants such as alkyl ether carboxylates.

In the composition of the present invention, the solubilizer is used in a weight ratio of solubilizer to silicone oil in the range of from 1:1 to 12:1, preferably 2:1 to 8:1. The amount of solubilizer is preferably 5 to 20 wt. %, more preferably 7 to 15 wt. % with respect to the total weight of the composition.

The anionic surfactant as component (c) is not a cryptoanionic surfactant and is preferably sodium lauryl ether sulfate, preferably having an average degree of ethoxylation of 1 to 3, more preferably 1 to 2.5, most preferably 2 to 2.5. The anionic surfactant is desirably contained in the composition in an amount of 3 to 15 wt. %, preferably 6 to 15 wt. %.

The weight ratio of component (b) to component (c) is within the range of 1:4 to 4:1, preferably 1:2 to 2:1, most preferably in the range of 6:7 to 7:6.

The total amounts of components (b) and (c) is within the range of 10 to 25 wt. % with respect to the total weight of the composition, preferably within the range of 12 to 20 wt. %. The total amount of wash active matter, that is, the total amounts of surfactants, contained in the composition of the present invention is preferably less than 25 wt. %. That is, if the composition contains surfactants other than components (b) and (c), the total amount of these surfactants and components (b) and (c) does desirably not exceed 25 wt. %.

The compositions of the present invention are optically transparent. According to the present invention, the term "optically transparent" means that the transmission of the composition in the visible region is at least 95%. The compositions of the present invention have preferably a transmission of more than 97%. The transmission is measured according to DIN 53995 using the Dr. Lange Liquid Tester LTM1 (supplied by Dr. Bruno Lange GmbH&Co. KG, Düsseldorf, Deutschland)

The viscosity of the composition of the present invention is preferably at least 1500 mPa·s, more preferably 2000–3000 mPa·s. The viscosity values indicated in the present invention are measured at 20° C. with a Brookfield viscosimeter LVT (supplied by Brookfield Engineering Laboratories Inc. Stoughton, Mass., USA) in accordance with DIN 1341 (spindle 2 at 30 rpm for viscosities in the range of up to 1000 mpa·s; spindle 3 at 12 rpm for viscosities in the range of 1000 to 7000 mPa·s; spindle 4 at 12 rpm for viscosities in the range of more than 7000 mPa·s).

The pH value of the composition of the present invention is preferably within the range of 5 to 8, more preferably 6 to 7.

Amphoteric surfactant which may be included in the composition of the present invention include ampholytes and betaines. Specific examples are alkyl amine oxides, alkyl betaines, alkyl sulphobetaines (sultaines), alkyl glycinates, alkyl carboxyglycinates, alkyl amphoacetates, alkyl amphopropionates, alklyamphoglycinates, alkyl amidopropyl betaines, alkyl amidopropyl- and hydroxysultaines. Particularly preferred amphoteric surfactants are alkyl sulphobetaines (sultaines), alklyamphoglycinates and alkyl amphoacetates. Even more preferred are alkyl hydroxysultaines, in particular lauryl hydroxysultaine.

Amphoteric surfactants are preferably present in a weight ratio of non-ionic or cryptoanionic solubilizer component to amphoteric surfactant in the range of 1:3 to 3:1. The total amount of amphoteric surfactant is preferably between 4 and 8 wt. % with respect to the total amount of the composition.

The composition of the present invention may optionally contain fatty alcohols having 6 to 22 carbon atoms.

The compositions of the present applications may also contain deposition polymers. Suitable deposition polymers are any which enhance deposition of the silicone oil on the intended site, i.e. the hair or the skin. The deposition polymers disclosed in EP-B-529 883 are preferably used.

The composition of the present invention may contain other surfactants such as cationic surfactants.

The composition of the present invention preferably also contains a vegetable oil. According to the present invention, the term vegetable oil means a mixture of saturated or unsaturated fatty acids having 6 to 22 carbon atoms, triglycerides thereof, esters thereof with alcohols having 6 to 22 carbon atoms, and the corresponding fatty alcohols having 6 to 22 carbon atoms. The vegetable oil may also be a terpinene-containing oil. Preferred examples of the vegetable oils to be used according to the present invention include evening prime rose oil, sesame oil and preferably jojoba oil, macadamia nut oil, tea tree oil, and avocado oil.

The vegetable oil is preferably contained in the composition of the present invention in a weight ratio of vegetable oil to silicone oil of 1:3 to 3:1, more preferably 1:1. The total amount of silicone oil and vegetable oil is preferably in the range of 2 to 6 wt. % with respect to the total weight of the composition.

If vegetable oil is present in the composition of the present invention, the hydrophobic silicone oil used is preferably a volatile hydrophobic silicone oil. Volatile hydrophobic silicone oils are silicone oils which evaporate from the hair surface at atmospheric pressure and room temperature.

The weight ratio of solubilizer to the total amount of silicone oil and vegetable oil is preferably in the range of 1:1 to 6:1, preferably 2:1 to 4:1.

The composition of the present invention may optionally contain further ingredients such as perfume, preservatives, thickeners, salts, and medically effective substances.

The preparation of the compositions of the present invention often requires a specific preparation method. By simply mixing the ingredients in any arbitrary order, the composition of the present invention may not always be obtained. This method will now be explained in more detail.

The method for preparing the compounds of the present invention comprises the steps:

(a) mixing silicone oil with solubilizer for the silicone oil in a weight ratio of solubilizer to silicone oil in the range of 1:1 to 10:1 at a temperature of 20° C. or less; and (b) adding anionic surfactant and stirring until an optically transparent composition is obtained.

Step (a) is generally carried out under gentle stirring. Low stirring energies are not only advantageous in view of energy costs, but particularly in view of the fact that less air is incorporated into the aqueous solution. Air is generally difficult to remove afterwards from the aqueous solution once incorporated and may cause stability problems.

In the following step (b), the anionic surfactant such as sodium lauryl ether sulfate is added and the resulting mixture is stirred until an optically transparent composition is obtained. The anionic surfactant is generally added in diluted form as aqueous solution in a concentration such that gelation is avoided in step (b). The concentration should preferably not exceed 30 wt.-%. Again, it is preferably only gently stirred in step (b).

In a further step (c), subsequent to step (b), the viscosity and the pH of the composition are preferably adjusted to the values indicated above. The viscosity of the composition prior to step (c) depends on the components used. If the viscosity is found to be insufficient, e.g., below 1500 mPa·s, thickeners such as non-ionic surfactants-type thickeners such as Aminol N, Cocamide DEA and Cocamide MEA and derivatives thereof or polymeric thickeners such as PEG-150 distearate, PEG-120 methyl glucose dioleate, or PEG-160 sorbitan isostearate may be added. However, the amount of polymeric thickeners should preferably not exceed an amount of 1 wt.-% with respect to the total weight of the composition. Higher amounts of polymeric thickener may cause an unpleasant sticky feeling on skin during application.

The pH value may be adjusted to the range of 5 to 8 by adding pH adjusting agents known in the field. Examples for pH adjusting agents include citric acid and NaOH.

If mixtures of non-ionic surfactants with amphoteric surfactants or cryptoanionic surfactants are used, the non-ionic surfactants are preferably added first, the resulting mixtures of silicone and non-ionic are gently stirred, followed by the addition of the amphoteric or cryptoanionic surfactant. Further ingredients such as perfume and preservations are usually added after step (c).

The compositions of the present invention show a number of beneficial properties in view of their high silicone content, and they may not only be used as personal care products such as shampoos, hair conditioners, hairdying agents, levelling agents, shower baths, liquid soaps and other cosmetic rinse-off products, but also in textile applications (softener) and plastic applications (plastic additives). The compositions are particularly useful as hair gloss shampoos, detangling shampoos, silky hair shampoos, fast drying shampoos, elderly people shampoos, colour care shampoos, special care shampoos.

EXAMPLES

In the Examples, all products used were obtained from Kao Chemicals Europe, unless indicated otherwise.

Example 1

Hair and Scalp Care Shampoo for Elderly People
Shampoo Recipe Recipe (≈25% Wash Active Matter; ≈29% Total Active Matter):

(1) 25% EMAL 228D (28% a.m.) (INCI: Sodium Laureth Sulfate)

(2) 18.5% BETADET S-20 (38% a.m.) (INCI: Lauryl Hydroxysultaine)

(3) 6% AMINOL N (91% a.m.) (INCI: PEG-4 Rapeseedamide)

(4) 6% LEVENOL C-201 (100% a.m.) (INCI: Glycereth-17 Cocoate)

(5) 1.5% Cyclomethicone (IUPAC Decamethylcyclopentasiloxane, supplied by Dow Corning)

(6) 1.5% Jojoba oil (7) 0.7% RHEODOL TW-IS399C (100% a.m.) (INCI: PEG-160 Sorbitan Isostearate) q.s. ad 100%: water, citric acid, perfume, preservative Shampoo Preparation:

(5) and (6) are stirred briefly (≈2 minutes) for intermixing, resulting in a clear liquid (4) is added and mixture is stirred briefly (≈3 minutes) for intermixing resulting in a turbid liquid (3) is added and stirred briefly (≈4 minutes) resulting in a clear liquid (2) is added and stirred briefly (≈3 minutes) resulting in a clear liquid of higher viscosity (1) is dissolved in 50% of the water and added together with preservative to above mixture and stirred for ≈3 minutes resulting in a clear liquid of lower viscosity (7) is dissolved in rest of the water at 50° C. & added together with perfume to above mixture and stirred for ≈8 minutes resulting in a clear liquid of suitable viscosity (≈1600 mPas at 20° C.)

pH-value is adjusted by citric acid (pH: 6–7)

Example 2

Hair Gloss Shampoo
Shampoo Recipe Recipe (23% Wash Active Matter; ≈26% Total Active Matter):

(1) 25% EMAL 228D (28% a.m.) (INCI: Sodium Laureth Sulfate)

(2) 18.5% BETADET S 20 (38% a.m.) (INCI: Lauryl Hydroxysultaine)

(3) 6% LEVENOL C-201 (100% a.m.) (INCI: Glycereth-17 Cocoate)

(4) 1.5% Phenyl Trimethicone (supplied by Dow Corning)

(5) 0.5% TETRANYL CO-40 (80% a.m.) (INCI: Dioleoylethyl Hydroxyethylmonium Methosulfate)( (6) 3% AMINOL N (91% a.m.) (INCI: PEG-4 Rapeseed amide)

(7) 0.7% RHEODOL TW-IS399C (100% a.m.) (INCI: PEG-160 Sorbitan Isostearate) q.s. ad 100%: water, sodium hydroxide, perfume, preservative Shampoo Preparation:

(5) is dissolved in (4) and stirred briefly (≈3 minutes) for intermixing, resulting in a clear mixture (3) is added and stirred for ≈3 minutes, resulting in a clear liquid (2) is added and stirred for ≈2 minutes resulting in a more viscous, turbid liquid after addition of (6) and stirring for ≈2 minutes, liquid becomes clear and less viscous again (1) is dissolved in 50% of the water and added together with preservative to above mixture and stirred for ≈3 minutes resulting in a clear liquid of lower viscosity (7) is dissolved in rest of the water at 50° C. and added together with the perfume to above mixture and stirred for ≈8 minutes resulting in a clear liquid of suitable viscosity (≈2400 mPas at 20° C.)

pH-value is adjusted by adding NaOH (50% a.m.)

Example 3

Hair Gloss Shampoo

Shampoo Recipe (≈19% Wash Active Matter; ≈22% Total Active Matter)
- (1) 25% EMAL 228D (28% a.m.) (INCI: Sodium Laureth Sulfate)
- (2) 5% AKYPO SOFT 70 BVC (70% a.m.) (INCI: Sodium Laureth-8 Carboxylate (and) Laureth-7)
- (3) 5% AKYPO SOFT 100 BVC (70% a.m.) (INCI: Sodium Laureth-11 Carboxylate (and) Laureth-10)
- (4) 1% jojoba oil
- (5) 1% Cyclomethicone ((IUPAC: Decamethylcyclopentasiloxane; supplied by Dow Corning)
- (6) 5% AMINOL N (91% a.m.) (INCI: PEG-4 Rapeseedamide)
- (7) 1% PEG-150 Distearate
- (8) 3% sodium chloride
q.s. at 100% : water, perfume, preservative, citric acid Shampoo Preparation:
- (4) and (5) are stirred briefly (≈5 minutes) for intermixing
- (2) and (3) are added and stirred until a homogeneous mixture is obtained (≈10 min)
- (7) and water are heated to 50° C. until (7) dissolved (≈20 min), followed by addition of (1) and stirring for ≈5 minutes, followed by addition of (6) (≈20 minutes stirring) and
- addition of preservative and perfume at a temperature below 30° C.
- this mixtures (containing the components (7), (1) and (6) is added to the mixture containing the components (2) to (5) obtained above and stirring is continued until a homogeneous mixture is obtained (≈20 min)
- the pH-value is adjusted by adding citric acid (pH: 6–7) and viscosity (≈3000 mPas at 20° C.) is adjusted by addition of (8)

Example 4

Fast Drying Hair Shampoo

Shampoo Recipe (≈24% Wash Active Matter; ≈27% Total Active Matter):
- (1) 12.5% EMAL 228D (28% a.m.) (INCI: Sodium Laureth Sulfate)
- (2) 20% AKYPO SOFT 100 BVC (70% a.m.) (INCI: Sodium Laureth-11 Carboxylate (and) Laureth-10)
- (3) 1% AKYPO QUAT 132 (70% a.m.) (INCI: Lauroyl PG-Trimonium Chloride)
- (4) 6% AMINOL A 15 (97% a.m.) (INCI: Trideceth-2 Carboxamide MEA)
- (5) 2% Cyclomethicone (IUPAC: Decamethylcyclopentasiloxane; supplied by Dow Corning)
- (6) 1% RHEODOL TW-IS399C liquid (61.5% a.m.) (PEG-160 Sorbitan Isostearate
- (7) 3.5% sodium chloride q.s. at 100%: water, perfume, preservative Shampoo Preparation:
- (4) and (5) are stirred briefly (≈2 minutes) for intermixing
- (2) is added while stirring and stirring is continued for 2 minutes
- (1) is dissolved in the water (to avoid gelation) and added to the above mixture while stirring (≈20 minutes), followed by addition of (3) and further stirring for ≈10 minutes.
- (6) is added, followed by adding perfume and preservative and
- viscosity adjustment by (7) (2000–3000 mPas at 20° C.).

Example 5

Foaminess

For demonstrating the low foaminess reducing effect of solubilized Cyclomethicone compared to emulsified one, a number of formulations were prepared as described above for Example 4:

Composition (2a):
- (1) 16% EMAL 228D (28% a.m.) (INCI: Sodium Laureth Sulfate)
- (2) 6% AKYPO SOFT 100 BVC (70% a.m.) (INCI: Sodium Laureth-11 Carboxylate (and) Laureth-10)
- (3) 6% AKYPO SOFT 70 BVC (70% a.m.)
- (4) 3% AMINOL A 15 (97% a.m.) (INCI: Trideceth-2 Carboxamide MEA)
- (5) ad 100%: water, perfume, preservative Composition (2b):
same basic composition as composition (2a), but additionally containing 2.5% of cyclomethicone Composition (2c):
- (1) 13% EMAL 228D (28% a.m.) (INCI: Sodium Laureth Sulfate)
- (2) 5% AKYPO SOFT 100 BVC (70% a.m.) (INCI: Sodium Laureth-11 Carboxylate (and) Laureth-10)
- (3) 5% AKYPO SOFT 70 BVC (70% a.m.)
- (4) 5% AMINOL A 15 (97% a.m.) (INCI: Trideceth-2 Carboxamide MEA)
- (5) ad 100%: water, perfume, preservative Composition (2d):
same basic composition as composition (2c), but additionally containing 2.5% of cyclomethicone The foaminess of the compositions (2a) to (2d) was determined by the Ross Miles Test (DIN 53902; 0.1% a.m.; 25° C.; 15° gh)). The differences in foaminess due to the presence of the silicone oil were found to be negligible (composition (2a): 197 mm; composition (2b): 187 mm; composition (2c): 186 mm; composition (2d): 177 mm) and comparable to a Sodium Laureth Sulfate/Cocamidopropyl Betaine based shampoo without silicone oil.

What is claimed is:

1. An optically transparent aqueous composition comprising
   (a) a hydrophobic silicone oil in an amount of 1–3 wt.-% with respect to the total weight of the composition;
   (b) a solubilizer for the silicone oil; and
   (c) an anionic surfactant;
wherein the weight ratio of component (b) to component (a) is in the range of 1:1 to 12:1; and wherein the total amount of the components (b) and (c) is in the range of 10–25 wt.-% with respect to the total weight of the composition.

2. The aqueous composition according to claim 1, wherein the solubilizer is a cryptoanionic surfactant, a non-ionic surfactant, a mixture of a non-ionic surfactant with an amphoteric surfactant, or a mixture of a non-ionic surfactant with a cryptoanionic surfactant.

3. The aqueous composition according to claim 2, wherein the solubilizer comprises an alkyl ether carboxylate derived from alkanols having 6 to 22 carbon atoms.

4. The aqueous composition according to claim 2, wherein the solubilizer is a mixture of alkyl ether carboxylate derived from alkanols having 6 to 22 carbon atoms with ethoxylated products derived from polyhydric alcohols.

5. The aqueous composition according to claim 2, wherein the solubilizer comprises an ethoxylated glyceride derived from carboxylic acids having 6 to 22 carbon atoms.

6. The aqueous composition according to claim 5, wherein the solubilizer comprises glycereth-17 cocoate.

7. The aqueous composition according to claim 2, wherein the solubilizer comprises a compound of the following formula (III):

wherein R is an alkyl group or alkenyl group having 6 to 22, preferably 12 to 18, more preferably 13 to 15 carbon atoms; R' is a hydrogen atom or an alkyl group or alkenyl group having 6 to 22, preferably 12 to 18, more preferably 13 to 15 carbon atoms; R" is a hydrogen atom or an alkyl group having 1 to 5 carbon atoms which is optionally hydroxylated, preferably a hydrogen atom, a methyl group, an ethyl group or a hydroxyethyl group; m has a value in the range of 1 to 10, preferably 1 to 3, most preferably 2; and n has a value in the range of 0 to 10, preferably 0 to 5.

8. The aqueous composition according to claim 7, wherein the solubilizer comprises a compound of the formula (III) wherein m is 2, n is 1, R represents an alkyl group having 13 to 15 carbon atoms; and both R' and R" represent a hydrogen atom.

9. The aqueous composition according to claim 1, wherein the hydrophobic silicone oil is a non-volatile silicone oil.

10. The aqueous composition according to claim 1, additionally containing a vegetable oil.

11. The aqueous composition according to claim 10, wherein the hydrophobic silicone oil is a volatile silicone oil.

12. The aqueous composition according to claim 2, wherein the amphoteric surfactant is lauryl hydroxysultaine.

13. The aqueous composition according to claim 2, wherein the amphoteric surfactant is present in an amount of 4 to 8 wt.-% with respect to the total weight of the composition.

14. The aqueous composition according to claim 1, wherein the anionic surfactant is sodium lauryl ether sulfate having an average degree of ethoxylation in the range of 1 to 3.

15. The aqueous composition according to claim 1, wherein the composition has a viscosity of at least 1500 mPa s.

16. The aqueous composition according to claim 1, wherein the composition has a pH value in the range of 5 to 8.

17. Method for preparing a composition according to claim 1, comprising the steps of:

(a) mixing silicone oil with a solubilizer for the silicone oil in a weight ratio of solubilizer to silicone oil in the range of 1:1 to 12:1 at a temperature of 20° C. or less; and (b) adding an aqueous solution of anionic surfactant and stirring until an optically transparent composition is obtained.

18. Hair shampoo comprising the composition of claim 1.

* * * * *